United States Patent [19]

Queuille

[11] 4,096,278

[45] Jun. 20, 1978

[54] ORGANIC DERIVATIVES OF MONTMORILLONITE FOR TREATING LIPID DISTURBANCES

[76] Inventor: André Queuille, 93, rue Denfert-Rochereau, 93130 Noisy-le-Sec, France

[21] Appl. No.: 810,678

[22] Filed: Jun. 27, 1977

[30] Foreign Application Priority Data

Jul. 1, 1976 France .................................. 76 20143

[51] Int. Cl.$^2$ ............................................ A61K 31/14
[52] U.S. Cl. .................................................... 424/329
[58] Field of Search ........................................ 424/329

[56] References Cited

U.S. PATENT DOCUMENTS 4,016,209  4/1977  Wagner et al. ...................... 424/329

OTHER PUBLICATIONS

Wilkinson–Chem. Abst., vol. 83 (1975) p. 48206n.
Lesshaft–Chem. Abst., vol. 67 (1967) pp. 120, 149k.

*Primary Examiner*—Sam Rosen
*Attorney, Agent, or Firm*—Stevens, Davis, Miller & Mosher

[57] ABSTRACT

Pharmaceutical compositions having hypocholesterolemic and hypolipemic activity comprising a dimethyl-dialkylammonium montmorillonite and use thereof in treatment of lipid disturbances.

4 Claims, No Drawings

ORGANIC DERIVATIVES OF MONTMORILLONITE FOR TREATING LIPID DISTURBANCES

This invention relates to pharmaceutical compositions containing, as an active principle, organic derivatives of montmorillonite.

It is known that certain organic derivatives of montmorillonite, and particularly the dimethyl-dialkylammonium montmorillonites, can be used as gelation agents for various organic media.

Thus the dimethyl-dialkylammonium montmorillonite sold by the National Lead Company under the registered trademark "Bentone" can, for instance, be used in the paint and varnish industry to modify the viscosity, rigidity, or plasticity of these paints and varnishes (Chemical Engineering, March 1952, pages 226–230).

Numerous other uses of these "Bentones" are described in the literature. Among them, one may mention the use of the "Bentones" as granulating agents and as binders in the preparation of tablets containing hydrolabile drugs (Amer. Jour. Pharm. 136 (5) p. 206–215, 1964). In the preparation of these tablets, the "Bentones" are used in amounts varying between 2 and 8% of the total weight of the tablets.

It has now been found that these dimethyl-dialkylammonium montmorillonites have remarkable pharmacological properties and, in particular, hypocholesterolemic and hypolipemic properties. These properties are illustrated further below wherein the usefulness of these products as drugs is shown.

Among these drugs, there are preferred, in particular, those which are characterized by the fact that the dimethyl-dialkylammonium has 10 to 50 carbon atoms.

The dimethyl-dialkylammonium montmorillonites can consist, for instance, of dimethyl-dipentadecylammonium montmorillonites, dimethyl-dihexadecylammonium montmorillonites, dimethyl-diheptadecylammonium montmorillonites, dimethyl-dioctadecylammonium montmorillonites, or mixtures of the above.

Among these drugs, most preferred are dimethyl-dioctadecylammonium montmorillonite (product sold under the registered trademark "Bentone 34" by the National Lead Company), and the mixture of dimethyl-dipentadecylammonium montmorillonite and dimethyl-dihexadecylammonium montmorillonite in proportions of 70% and 30% respectively (product sold under the registered trademark "Bentone 38" by the National Lead Company).

These drugs are used, for instance, in the treatment or prevention of lipid disturbances associated with atherosclerotic manifestations, hypercholesterolemias, with or without xanthomatosis, hypertriglyceridemias, or hyperlipemias, whether acute or chronic.

The customary dose, which varies in accordance with the product used, the patient treated, and the ailment in question, may for instance be from 2 g to 30 g per day, orally in humans.

Another object of the present invention is to provide pharmaceutical compositions which contain at least 15% dimethyl-dialkylammonium montmorillonite as the active principle.

Among the preferred pharmaceutical compositions of the invention mention may be made, in particular, of:

(a) those characterized by the fact that they contain as an active principle 20 to 90% dimethyl-dioctadecylammonium montmorillonite, and (b) those characterized by the fact that they contain as an active principle 20 to 90% of a mixture formed of 70% dimethyl-dipentadecylammonium montmorillonite and 30% dimethyl-dihexadecylammonium montmorillonite.

As drugs, the dimethyl-dialkylammonium montmorillonites can be incorporated in pharmaceutical compositions intended for the digestive tract.

These pharmaceutical compositions may, for instance, be solid or liquid and be in the pharmaceutical forms currently used in human medicine such as for instance simple or effervescent tablets, lozenges, granules, suspensions, jellies and jams. They are prepared in accordance with customary methods. The active principle or principles can be incorporated therein with the excipients customarily used in these pharmaceutical compositions such as talc, gum arabic, lactose, starch, magnesium stearate, aqueous or non-aqueous vehicles, fats of animal or vegetable origin, paraffin derivatives, glycols, various wetting, dispersing, or emulsifying agents, and preservatives.

As indicated in the literature, the dimethyl-dialkylammonium montmorillonites can be obtained, for instance, by reacting a montmorillonite in the sodium form with the desired quaternary ammonium compound in chloride form.

Various examples of the manner of carrying out the invention will now be given, by way of illustration and not of limitation.

EXAMPLE 1

20 g sachets were prepared having the following formulation:

| | |
|---|---|
| -Bentone 34 | 10 g |
| -Pluronic F 38 | 0.05 g |
| -polyvinyl pyrrolidone | 0.40 g |
| -caramel flavoring | 0.15 g |
| -granulated sugar | 9.40 g |

The Bentone 34 (dimethyl-dioctadecylammonium montmorillonite), the granulated sugar and the caramel flavoring are introduced into a mixer.

It is wetted with an alcoholic solution of polyvinyl pyrrolidone and Pluronic F 68 (condensation polymer of ethylene and propylene oxides). It is granulated, dried, and the grains sized. The granulate obtained can then be placed in 20 g sachets.

EXAMPLE 2

15 g sachets were prepared having the following formulation:

| | |
|---|---|
| -Bentone 34 | 10 g |
| -Pluronic F 68 | 0.05 g |
| -polyvinyl pyrrolidone | 0.40 g |
| -caramel flavoring | 0.15 g |
| -granulated sugar | 4.40 g |

The Bentone 34 (dimethyl-dioctadecylammonium montmorillonite), the granulated sugar and the caramel flavoring are introduced into a mixer.

The mixture is wetted with an alcoholic solution of polyvinyl pyrrolidone and Pluronic F 68 (condensation polymer of ethylene and propylene oxides). It is granulated and dried and the grains sized.

The granulate obtained can then be placed in 15 g sachets.

EXAMPLE 3

20 g sachets were prepared of the following formulation:

| -Bentone 38 | 10 g |
| -Pluronic F 68 | 0.05 g |
| -polyvinyl pyrrolidone | 0.40 g |
| -caramel flavoring | 0.15 g |
| -granulated sugar | 9.40 g |

The Bentone 38 (mixture of dimethyl-dipentadecylammonium montmorillonite and dimethyl-dihexadecylammonium montmorillonite in proportions of 70% and 30% respectively), the granulated sugar and the caramel flavoring are introduced into a mixer.

The mixture is wetted with an alcoholic solution of polyvinyl pyrrolidone and Pluronic F 68 (condensation polymer of ethylene and propylene oxides). It is granulated and dried and the grains sized.

The granulate obtained can then be placed in 20 g sachets.

Pharmacological Study (1) Effects of Bentone 38 on the Fecal Excretion of Fats

Wistar rats of about 250 g are given for 8 days a feed composed of a semisynthetic standard ration (U.A.R. 210) containing 5.5% lipids. At the end of this period of 8 days the animals are weighed, distributed at random in two lots (control lot, treated lot) and placed in individual metabolic cages with standard rations for 3 days. The feces are collected quantitatively and weighed, and the lipids are extracted by means of methanol-chloroform. The determinations of cholesterol and total fatty acids in the feces are effected in accordance with the customary techniques (first stage).

The animals of each lot are then placed back in collective cages. The animals of the control lot then receive the aforementioned standard ration for 16 days. During the same time, the animals of the treated lot receive the said standard ration plus 2.5 g of Bentone 38 per kg. At the end of this period of 16 days, the animals are placed in individual metabolic cages in order to collect their feces for 3 days, the animals receiving their respective rations during this time (2nd stage).

The determinations of the cholesterol and the total fatty acids in the feces are carried out in the same manner as at the end of the first stage.

The results obtained with the animals of the control lot are set forth in Table 1 below:

Table 1

| Animals of the control lot | Weight of the animals in g | Weight of the 24 hr. feces in g | Cholesterol mg/24 hr. | Total fatty acids mg/24 hr. |
|---|---|---|---|---|
| After 8 days of standard rations (1st stage) | 258 ± 3.2 | 1.87 ± 0.09 | 2.98 ± 0.14 | 97.84 ± 5.6 |
| After 16 days of standard rations (2nd stage) | 328 ± 4.0 | 2.12 ± 0.09 | 3.27 ± 0.18 | 105 ± 3.25 |

Table 1-continued

Average of 11 rats ± standard error.

The results obtained with the animals of the treated lot are set forth in Table 2 below:

Table 2

| Animals of the treated lot | Weight of the animals in g | Weight of the 24 hr. feces in g | Cholesterol mg/24 hr. | Total fatty acids mg/24 hr. |
|---|---|---|---|---|
| After 8 days of standard rations (1st stage) | 261 ± 3.0 | 2 ± 0.12 | 2.91 ± 0.23 | 94.46 ± 4.62 |
| After 16 days of standard rations containing 2.5 g of Bentone 38 (2nd stage) | 334 ± 13.7 | 1.96 ± 0.08 | 4.37 ± 0.17 | 113.84 ± 6.5 |

Average of 10 rats ± standard error.

The results obtained show that the administration of the Bentone 38 produces in the treated animals a significant increase in the excretion of fatty acids and cholesterol.

(2) Effect of Bentone 34 and Bentone 38 on the Intestinal Absorption of Lipids in Rats Three lots of 15 rats of an average weight of 200 g are fed for 3 weeks with a standard ration enriched by 10% lard, 0.5% cholesterol and 0.5% bileacids.

A first lot of animals, maintained with this hyperlipemic and steatogenous ration for 3 weeks is considered as a control.

The other two lots receive, for the three weeks, the same ration to which the products studied have been added, namely 2% Bentone 34 and 2% Bentone 38, respectively. These quantities are calculated so that the animals receive a daily dose of about 400 mg of product per rat per day.

The weights of the animals are checked at the beginning and end of the experiment. The hepatic and plasmatic lipids are analyzed at the time of sacrifice after three weeks of experiments.

The determination of the hepatic lipids gave the results set forth in Table 3 below:

Table 3

| Animals | Total lipids mg/g | Triglycerides mg/g | Cholesterol mg/g |
|---|---|---|---|
| Controls | 211.70 ± 0.48 | 56.79 ± 2.98 | 16.00 ± 0.33 |
| Treated with Bentone 34 | 124.19 ± 5.27 | 24.37 ± 1.44 | 18.53 ± 0.65 |
| Treated with Bentone 38 | 153.34 ± 3.92 | 36.83 ± 2.51 | 17.43 ± 0.23 |
| Normal rat | 37 | 5.6 | 4.5 |

Average of 15 rats ± standard error.

The histological examination of hepatic tissue sections stained with Masson Trichrome and Red Oil furthermore show an extensive steatosis in the control animals and in the treated animals. However, it is less pronounced in the animals treated with the Bentone 34.

The determination of the plasmatic lipids gave the results set forth in Table 4 below:

Table 4

| Animals | Total lipids mg/100 ml | Triglycerides mg/100 ml | Cholesterol mg/100 ml |
| --- | --- | --- | --- |
| Controls | 741.10 ± 47.2 | 114.00 ± 7.8 | 251.70 ± 11.02 |
| Treated with Bentone 34 | 519.55 ± 29.06 | 88.00 ± 7.7 | 186.67 ± 11.37 |
| Treated with Bentone 38 | 663.9 ± 23.6 | 107.00 ± 7.74 | 185.67 ± 7.07 |
| Normal rat | 350 | 100 | 70 |

Average of 15 rats ± standard error.

The results obtained with the compounds studied show that they exert a marked protective effect against the development of hyperlipemia and of hepatic steatosis caused by a ration enriched by triglycerides and cholesterol.

If one takes into account the considerable charge of lipids and cholesterol in the ration, the absorption of which was facilitated by the addition of bile salts, it becomes obvious that the compounds studied have the property of preventing the intestinal absorption of cholesterol and lipids.

What is claimed is:

1. A method of treating and preventing lipid disturbances comprising administering to the patient a hypocholesterolemically and hypolipemically effective amount of dimethyl-dialkylammonium montmorillonite.

2. A method according to claim 1 wherein the dimethyl-dialkylammonium montmorillonite contains 10 to 50 carbon atoms.

3. A method according to claim 2 wherein the dimethyl-dialkylammonium montmorillonite is dimethyl-dioctadecylammonium montmorillonite.

4. A method according to claim 2 wherein the dimethyl-dialkylammonium montmorillonite consists of a mixture of dimethyl-dipentadecylammonium montmorillonite and dimethyl-dihexadecylammonium montmorillonite in proportions of 70% and 30%, respectively.

* * * * *